United States Patent [19]

Scheben

[11] 4,097,533
[45] Jun. 27, 1978

[54] LIQUID PHASE PROCESS FOR THE PRODUCTION OF AROMATIC ALDEHYDES

[75] Inventor: John A. Scheben, Erlanger, Ky.

[73] Assignee: National Distillers and Chemical Corporation, New York, N.Y.

[21] Appl. No.: 743,435

[22] Filed: Nov. 19, 1976

[51] Int. Cl.² .............................................. C07C 45/00
[52] U.S. Cl. .................. 260/599; 260/600 R; 260/524 R; 560/51; 260/592; 260/591; 260/346.3
[58] Field of Search ................ 260/599, 524 R, 600 R

[56] References Cited

U.S. PATENT DOCUMENTS

| | | | |
|---|---|---|---|
| 3,162,683 | 12/1964 | Jones et al. | 260/599 X |
| 3,385,897 | 5/1968 | Vanderwerff | 260/599 |
| 3,488,395 | 1/1970 | Hooper | 260/599 X |
| 3,671,582 | 6/1972 | David et al. | 260/599 X |

*Primary Examiner*—Bernard Helfin
*Attorney, Agent, or Firm*—Kenneth D. Tremain

[57] ABSTRACT

A process is described for the preparation of aromatic aldehydes such as benzaldehyde and substituted benzaldehydes by the liquid phase oxidation of toluene or substituted toluenes in the presence of a catalyst comprising phosphoric acid and a catalytically effective amount of palladium metal, and a sulfur, phosphorus or nitrogen modifier.

10 Claims, No Drawings

LIQUID PHASE PROCESS FOR THE PRODUCTION OF AROMATIC ALDEHYDES

BACKGROUND OF THE INVENTION

Current industrial practice for the oxidation of toluene to benzaldehyde utilizes a uranium oxide/molybdenum oxide catalyst at about 500° C. (Faith et al., Industrial Chamicals, 3rd Edition, John Wiley & Sons, Inc., New York 1965). An improved process for the production of benzaldehyde is described in U.S. Pat. No. 3,946,067 which involves vapor phase oxidation at temperatures of less than about 250° C. In this process, the aryl alkyl compound is oxidized in the presence of a catalyst containing palladium metal and phosphoric acid. The phosphoric acid is required for the successful operation of this process.

U.S. Pat. No. 3,947,495 describes the use of sulfur modifiers with palladium catalysts to retard tar formation on the catalyst system in the vapor phase oxidation of propylene or isobutylene to acrylic or methacrylic acid, thus extending catalyst life and increasing reaction rates.

There are numerous references in the prior art to the catalytic oxidation of toluene to benzoic acid carried out batchwise in liquid phase stirred reactors.

For example, U.S. Pat. No. 3,865,870 describes the conversions of methylated benzenes to corresponding carboxylic acids by oxidation with air in aqueous media over silver or platinum family metal catalysts, including palladium metal catalysts. U.S. Pat. No. 3,679,740 describes the use of ammonia and amines to improve yields of aromatic acids obtained by oxidation of alkylbenzenes with oxygen over transition metal salt catalysts. However, the selective oxidation of toluene to benzaldehyde in liquid phase has only been accomplished by carrying out the oxidation in the presence of an alkanol using a metal salt catalyst (U.S. Pat. No. 3,732,314) or in the presence of an aliphatic aldehyde, e.g., acetaldehyde, optionally in the presence of a transition metal compound catalyst (U.S. Pat. No. 3,931,330). It has now been found that toluene and other aryl alkyl compounds can be selectively catalytically oxidized to benzaldehyde and other aromatic aldehydes using a phosphoric acid-palladium catalyst and certain sulfur, phosphorus or nitrogen modifiers. It is indeed surprising that high selectivity can be obtained using the present inventive process since attempted oxidations of toluene to benzaldehyde using otherwise identical catalyst systems and reaction conditions, but in the absence of the aforesaid promoters, more specifically defined hereinafter, has led to extremely low conversions to benzaldehyde and, surprisingly, concomitant low oxygen conversions. The present process, however, provides high selectivity for benzaldehyde production, with significant yields of benzaldehyde realized with concomitant high oxygen conversions. The yields of benzaldehyde realized by the present invention afford a process which is amenable to commercial production of benzaldehyde, a valuable chemical product and intermediate.

SUMMARY OF THE INVENTION

This invention relates to the selective liquid phase oxidation of aryl alkyl compounds to the corresponding aromatic aldehydes and, more particularly, relates to such a process utilizing a phosphoric acid-palladium catalyst and certain sulfur, phosphorus and nitrogen modifiers.

The starting compound for the present process is a toluene compound, i.e. toluene and substituted toluenes wherein the substituent may be lower alkyl and alkoxy, aryl, aryloxy, carboxy, carbo (lower) alkoxy, or acyl groups derived from lower alkanoic and aryl carboxylic acids. The number of substituents can range from one to five on the aromatic ring, but preferably is not greater than two. Representative compounds include toluene, xylene, cymene, mesitylene, durene, pentamethylbenzene, hexamethylbenzene, methylnaphthalene, p-phenyltoluene, 2,2-bis (p-tolyl) propane, p-phenoxytoluene, di-p-tolyl ether, 2,5-dimethoxytoluene, methyl p-toluate, p-toluic acid, p-methyl benzophenone, 4-methylphthalic anhydride, and the like.

Where the toluene starting compound contains lower alkyl substituents, especially methyl substituents, oxidation of such groups can occur. For example, the oxidation of xylene will yield, as the primary product, tolualdehyde, but can also result in benzene dialdehyde. Thus, oxidation of p-xylene will yield as primary product p-tolualdehyde, and as secondary oxidation product, terephthalaldehyde. The preferred compound for use in this process is toluene.

In the following description of preferred embodiments, reference is principally made to the oxidation of toluene, the preferred starting compound, to benzaldehyde, but it should be understood that the process description is applicable to substituted toluenes, as hereinbefore described.

DESCRIPTION OF THE PREFERRED EMBODIMENTS

In accordance with the present invention, an aryl alkyl compound is oxidized in the liquid phase by molecular oxygen in the presence of a catalyst composition containing palladium metal, and certain sulfur, phosphorus or nitrogen modifiers to form the desired aromatic aldehyde.

Toluene, the preferred starting compound may be used in pure form or in diluted form, such as, for example, in the form of a mixture containing up to about 50% of diluents, usually inert hydrocarbons, e.g., heptane, hexane, cyclohexane or benzene.

The oxidizing agent employed can be pure oxygen or an oxygen containing gas mixture such as air or air enriched with oxygen and the gas mixture may also contain inert diluent gas such as carbon dioxide, or nitrogen. It has also been found desirable to additionally incorporate water and phosphoric acid in the reaction mixture.

The amount of oxidizing agent employed is not excessively critical since the product, benzaldehyde, can be separated from the liquid reaction product and unreacted toluene recycled. Thus, stoichiometric proportions of oxygen, i.e., one mole of oxygen per mole of toluene, can be used. As desired, the amount of oxygen incorporated into the reaction can be from about 1 to about 99 mole percent in admixture with from about 1 to about 99 mole percent of toluene which may be in the flammability range of the mixture. In general, it is preferred to operate an oxygen-lean or rich system to avoid potential flammability. For example, there can be employed toluene to oxygen to nitrogen mole ratios of 0.1:2:7.9 which would provide about 10 mole percent toluene in the vapor over the reaction mixture. Alternatively, with a corresponding ratio of about 4:1:5, there would be about 40 mole percent toluene in the vapor over the reaction mixture. Thus, it is possible using such ratios to provide either oxygen-lean or oxygen rich systems by controlling the ratio of toluene to oxygen in the reaction with attention to the upper and lower flammability range of toluene in oxygen which are encompassed by the broad range specified.

The liquid phase reaction is carried out at elevated temperatures, preferably from about 140° to about 300° C., and most preferably from about 160° to about 260° C. Sufficient pressure is used to maintain the liquid phase at the reaction temperature and, in general, the pressure will be about 10 to 2500 psig, and preferably about 80 to 2000 psig.

The catalyst employed contains a catalytically effective amount of palladium metal suitably supported on a conventional catalyst carrier, such as, e.g., carbon, silica, alumina, titania, zirconia, ion exchange resin, diatomaceous earth, glass beads or the like. The palladium metal can be used along or can be admixed, alloyed or in solid solution with a Group 1B or Group VIII metal. Such other metals include gold, silver, platinum, rhodium, ruthenium, iridium, as well as mixtures thereof.

The palladium metal is incorporated in amounts of about 0.1 to 20 percent, preferably from about 0.5 to 6 percent by weight of the supported catalyst. If another metal is present in the catalyst composition, it will be incorporated in an amount ranging from about 1 to 500 percent, preferably from about 10 to 200% by weight based on the weight of the palladium.

Apparently, phosphoric acid is an essential component of the catalyst system of the present process, since palladium catalyst systems which do not contain phosphoric, or other strong, inert acid, such as phosphosilicic acid, are not practical in this process. Phosphoric acid is incorporated at levels of at least 1% and up to 1000% by weight of the supported catalyst, the preferred levels being from about 200 to about 600% by weight of the supported catalyst. The phosphoric acid may be added along with the catalyst by any convenient method. Thus, phosphoric acid can be added initially along with the supported catalyst or to the catalyst or to the catalyst support before impregnation with the palladium catalyst, or to the supported palladium catalyst, as desired. Alternatively, the phosphoric acid can be metered into the reaction vessel during the course of the reaction.

It has been found desirable in accordance with the present invention to additionally incorporate water in the reaction mixture. Whether water acts as a catalyst promoter or otherwise participates in a complex reaction with the substrate is not presently understood. While water, for purposes of convenience is referred to hereinafter as a catalyst promoter, it will be understood that its use in the process is contemplated, irrespective of the actual mechanism by which it may act.

The water may be added to the reaction medium by any convenient method or can be metered, conveniently with phosphoric acid, to the reaction vessel during the course of the reaction. The amounts of water present can be as little as about 1% and can range up to 1000% by weight of the catalyst and support, with the preferred range being from about 200 to about 600% by weight of the supported catalyst.

The catalyst system also contains a small amount of a sulfur, phosphorus or nitrogen modifier. The modifiers of the present invention include:

(a) compounds of the formula, R—Z in which R is alkyl, aryl, aralkyl or alkaryl of up to about 8 carbon atoms and Z is —SH, —SR′, —SSR′, R′SO—, R′SO$_2$— or

wherein R″ is H or lower alkyl and R′ has the same meaning as R;

(b) cyclic compounds containing a hetero sulfur atom;

(c) thiourea and N-lower alkyl thiourea;

(d) tertiary amines containing up to about 10 carbon atoms;

(e) R$_3$PO$_3$ and R$_3$PO$_4$ wherein R has the same meaning as above;

and mixtures thereof.

The modifiers to be employed in accordance with the invention include:

thiols, such as alkyl, aryl, alkaryl and aralkyl thiols exemplified by propanethiol, pentanethiol, tolylthiol, phenylthiol, benzylthiol and phenethylthiol, as well as the corresponding sulfides, disulfides, sulfones and sulfoxides, exemplified by diphenyl sulfide, diethyl disulfide, dimethyl sulfoxide, dipropyl sulfone, dibenzyl sulfide, diphenyl disulfide, diethyl sulfide, and the like;

thioamides, such as thioalkanoamides exemplified by thioacetamide, N-methyl thioacetamide, thiocaproamide and N,N-dimethyl thiopropionamide;

sulfur-heterocyclic compounds including thiophene, phenothiazine, thiazole, benzothiophene, and the like, and corresponding sulfones and sulfoxides thereof;

tertiary amines e.g., trialkyl amines such as dimethyl pentyl amines, triethyl amine and trimethyl amine; dialkyl aryl amines such as N,N-dimethyl aniline and N,N-diethyl toluidine; dialkyl aralkyl amines such as N,N-dimethyl benzyl amine; and pyridine and homologs thereof such as the picolines;

thiourea and N-methyl thiourea; and organic esters of phosphorus and phosphoric acids, such as triethyl, triphenyl and tricresyl phosphites and phosphates.

Mixtures of the modifiers may be employed.

The preferred modifiers are the thioalkanoamides, dialkyl disulfides and dialkyl sulfoxides, especially those of a carbon content of from 2 to about 6 carbon atoms. Specific preferred modifiers are thioacetamide, diethyl disulfide and dimethyl sulfoxide.

The modifiers are added to the reaction system in any convenient manner. They may be added along with the catalyst or in the materials charge, or added separately before the material charge. The amount of modifier can vary appreciably. As little as about 0.01% by weight, based on the supported catalyst weight, will be effective. In general, the amount of modifier can range up to about 1000% of the supported catalyst weight but it usually is preferred to use from about 5 to about 600 weight percent.

The catalyst utilized in the present invention can be prepared by conventional means e.g., as described in U.S. Pat. No. 3,946,067, incorporated herein by reference for the disclosure of catalyst preparation, but the precise manner in which the catalyst is prepared does not form a part of this invention.

Preferably, the catalyst is employed in finely divided form, i.e. in a form to provide a high surface area of the catalyst, to permit intimate contact with the liquid reaction system. Thus, commercial palladium on silica available in bead form is ground to a fine powder and used as such in the present process to obtain best results.

The present process is adaptable to being carried out in batch, semi-continuous and continuous operation in an enclosed reaction zone. Recycle of recovered unreacted toluene, as well as solvents and recovered phosphoric acid, can be readily effected using standard techniques.

After the oxidation reaction, the desired benzaldehyde is separated by any convenient means such as by distillation and/or extraction and the like. Any unreacted feed material separated from the recovered effluent can be recycled for further reaction. Benzoic acid is a valuable by-product obtained from the reaction mixture.

The following Examples are provided to further illustrate the present process. As used throughout this specification and claims, all parts and percentages are by weight and all temperatures in degrees Centigrade unless otherwise specified. Also, as used in these Examples, percent oxygen conversion and percent yield are calculated according to the following:

$$\% \text{ O}_2 \text{ conversion} = \frac{\text{moles O}_2 \text{ fed} - \text{moles O}_2 \text{ vented} \times 100}{\text{moles O}_2 \text{ fed}}$$

$$\% \text{ yield} = \% \text{ O}_2 \text{ conversion} \times 100 \times$$

$$\left[ \frac{\text{moles of benzaldehyde}}{\text{moles benzaldehyde} + (1.5 \times \text{moles benzoic acid}) + 1.3 \text{ (moles CO}_2)} \right]$$

EXAMPLE 1

A 78 ml. 316 stainless steel reactor is charged with the following:

|  | millimoles |
|---|---|
| toluene | 37 |
| water | 28 |
| $H_3PO_4$ | 8 |
| Pd (as 5% Pd on silica) | 0.1 |

The reactor is pressurized with air to 1,000 psig and heated at 200° C for 1 hour. The excess pressure is discharged after the reactor cooled to ambient temperature. The reaction products are separated from the catalyst by filtration and analyzed by gas-liquid chromatography. The oxygen conversion is 26% and the yield of benzaldehyde is 6%.

EXAMPLE 2

The procedure of Example 1 is repeated except for the addition of the following modifiers with the results indicated:

|  | mM | % $O_2$ conversion | % $O_2$ yield to benzaldehyde |
|---|---|---|---|
| diethyl disulfide | 0.08 | 63 | 41 |
| dimethyl sulfoxide | 0.14 | 50 | 32 |
| di(n-propyl)sulfone | 0.15 | 50 | 19 |
| thioacetamide | 0.4 | 87 | 29 |
| triethyl phosphate | 1.0 | 68 | 20 |
| triethyl phosphite | 1.2 | 96 | 30 |
| pentanethiol | 0.1 | 96 | 33 |
| thiophene | 0.1 | 74 | 36 |
| thiourea | 0.5 | 96 | 21 |
| phenothiazine | 0.2 | 30 | 15 |
| diphenyl sulfide | 0.01 | 37 | 15 |

EXAMPLE 3

The procedure of Example 2 is repeated using carbon, alumina and diatomaceous earth in place of silica with comparable results.

EXAMPLE 4

Following the procedure of Example 2 the following reactants are selectively oxidized to the corresponding aromatic aldehydes:

| o-xylene | o-tolualdehyde |
| p-xylene | p-tolualdehyde |
| p-cymene | p-isopropylbenzaldehyde |
| m-methoxytoluene | m-methoxybenzaldehyde |
| methyl p-toluate | p-carbomethoxybenzaldehyde |

EXAMPLE 5

Example 2 is repeated except that the catalyst additionally contained 0.1 percent gold. Comparable results are obtained.

What is claimed is:

1. A process for the preparation of aromatic aldehydes which comprises contacting at a temperature of from about 140° to about 300° C toluene or a substituted toluene in which the substituent is lower alkyl or lower alkoxy in the liquid phase with oxygen in the presence of a catalyst comprising at least about 1% by weight of phosphoric acid and of water and a catalytically effective amount of palladium and at least about 0.01% by weight of a modifier selected from the group consisting of:

(a) compounds of the formula, R-Z in which R is alkyl, aryl, aralkyl or alkaryl of up to about 8 carbon atoms and Z is —SH, —SR′, —SSR′, R′SO—, R′SO$_2$— or

wherein R″ is H or lower alkyl and R′ has the same meaning as R;

(b) cyclic compounds containing a hetero sulfur atom selected from the group consisting of thiophene, phenothiazine, thiazole and benzothiophene and sulfones and sulfoxides thereof (c) thiourea and N-lower alkyl thiourea;

(d) tertiary amines containing up to about 10 carbon atoms; and (e) $R_3PO_3$ and $R_3PO_4$ wherein R has the same meaning as above, said percents by weight being based on the weight of the supported catalyst.

2. Process according to claim 1 wherein said modifier is diphenyl sulfide, pentanethiol, diethyl disulfide, thioacetamide, thiourea, thiophene, dimethyl sulfoxide, di-n-propyl sulfone, phenothiazine, triethylamine, triethylphosphite, or triphenylphosphate.

3. Process according to claim 1 wherein said palladium is admixed, alloyed or in solid solution with a Group 1B or Group VIII metal.

4. Process according to claim 1 wherein the reaction mixture contains water in amounts from about 200 to about 600 weight percent of the supported catalyst.

5. Process according to claim 1 wherein said phosphoric acid is present in amount ranging from about 200 to about 600 weight percent based on the supported catalyst.

6. Process according to claim 1 wherein said modifier is present in an amount of from about 5 to about 600 weight percent of supported catalyst.

7. The process of preparing benzaldehyde by oxidizing toluene in the liquid phase with molecular oxygen in the presence of a supported catalyst comprising phosphoric acid and a catalytically effective amount of palladium, at least about 0.1% by weight of water and in the presence of at least about 0.01% by weight of a modifier selected from the group consisting of:

(a) compounds of the formula, R-Z in which R is alkyl, aryl, aralkyl or alkaryl of up to about 8 carbon atoms and Z is —SH, —SR', —SSR', R'SO—, R'SO$_2$— or

wherein R" is H or lower alkyl and R' has the same meaning as R;

(b) cyclic compounds containing a hetero sulfur atom selected from the group consisting of thiophene, phenothiazine, thiazole and benzothiophene and sulfones and sulfoxides thereof (c) thiourea and N-lower alkyl thiourea;

(d) tertiary amines containing up to about 10 carbon atoms; and (e) R$_3$PO$_3$ and R$_3$PO$_4$ wherein R has the same meaning as above, said percents by weight being based on the weight of supported catalyst.

8. Process according to claim 7 wherein said modifier is dimethyl sulfoxide, thioacetamide or diethyl disulfide.

9. Process according to claim 7 wherein said palladium is supported on a carrier therefor.

10. Process according to claim 9 wherein said carrier is a silica carrier.

* * * * *